United States Patent
Karna

(10) Patent No.: US 9,872,796 B1
(45) Date of Patent: Jan. 23, 2018

(54) MINIMAL CONTACT SPLINTING FOR MALLET FINGER DEFORMITY

(71) Applicant: Ratish K. Karna, Nassau (BS)

(72) Inventor: Ratish K. Karna, Nassau (BS)

( * ) Notice: Subject to any disclaimer, the term of this patent is extended or adjusted under 35 U.S.C. 154(b) by 561 days.

(21) Appl. No.: 14/594,263

(22) Filed: Jan. 12, 2015

Related U.S. Application Data

(63) Continuation-in-part of application No. 14/048,275, filed on Oct. 8, 2013, now abandoned.

(51) Int. Cl.
*A61F 5/05* (2006.01)
*A61F 5/058* (2006.01)

(52) U.S. Cl.
CPC ................. *A61F 5/05875* (2013.01)

(58) Field of Classification Search
CPC .............. A61F 5/05875; A61F 5/05866; A61F 2007/0046; A61F 2013/0048; A61F 13/068; A61F 2/42; A61F 2/4225; A61F 2002/423; A61F 2002/4235; A61F 2/4606; A61F 2002/6621; A61F 2002/6628; A61F 5/019; A61F 5/0585; A61F 2/588; A61F 5/0118; A61F 5/013; A61F 5/10; A61F 13/10; A61F 13/104; A61F 13/105
USPC .......................................................... 602/22
See application file for complete search history.

(56) References Cited

U.S. PATENT DOCUMENTS

| | | | | |
|---|---|---|---|---|
| 5,681,269 | A * | 10/1997 | Basaj ................... | A61F 5/05866 602/21 |
| 5,848,983 | A * | 12/1998 | Basaj ................... | A61F 5/05866 602/21 |
| 2010/0262057 | A1* | 10/2010 | Chandrasekar ..... | A61F 5/05875 602/22 |
| 2012/0289876 | A1* | 11/2012 | Hegland ............... | A61F 5/0118 602/22 |
| 2012/0289877 | A1* | 11/2012 | Hegland ............ | A61F 5/05875 602/22 |
| 2015/0094636 | A1* | 4/2015 | Miyazawa .............. | A61F 5/013 602/22 |

* cited by examiner

*Primary Examiner* — Tarla Patel
(74) *Attorney, Agent, or Firm* — Glenn E. Gold, P.A.; Glenn E. Gold; David Colls

(57) ABSTRACT

A splinting apparatus treating a flexion deformity of a finger includes a phalangeal bracket and a first anchoring ring fixedly attached thereto and positioned on the finger proximally of the deformity, a nail bracket and a second anchoring ring fixedly attached thereto and positioned on the finger distally of the deformity, and a rigid connecting rod extending between, and fixedly attached to at least one of the phalangeal and nail brackets so as to couple the brackets in a spaced apart positional relationship to each other along the finger relative to the flexion deformity. Each of the first and second anchoring rings is formed from an elongated narrow band integrally connected respectively with one of the phalangael and nail brackets and having first and second band extensions being bendable in opposite directions circumferentially around the finger so as to overlap and secure to one another.

20 Claims, 13 Drawing Sheets

MINIMAL CONTACT SPLINTING FOR MALLET FINGER DEFORMITY

CROSS REFERENCE TO RELATED APPLICATION

This non-provisional patent application is a continuation-in-part of co-pending U.S. non-provisional utility patent application Ser. No. 14/048,275 filed on Oct. 8, 2013, which is hereby incorporated-by-reference herein in its entirety.

FIELD OF THE INVENTION

The present invention relates to treating, non-surgically by splinting, a mallet finger deformity, and more particularly, is concerned with an apparatus, method and system for treating the finger by splinting with minimal skin contact the distal interphalangeal (DIP) joint in a neutral or slight hyperextension position.

BACKGROUND OF THE INVENTION

A mallet finger deformity of a finger occurs due to rupture or avulsion of Extensor Digitorum Communis (EDC) tendon at its insertion on the distal phalanx. In other words, it is a condition of a finger where the tendon in the outermost joint of the finger is ruptured, principally due to jamming of the finger at its outer tip, causing the tip of the finger to droop and thereafter making it difficult to fully straighten the finger. It is generally treated non-surgically with splints that immobilize the DIP joint in a neutral or slight hyperextension position. The splint is required to be on for four to six weeks continuous followed by two weeks night time only. Surgical treatment is reserved for mallet finger deformity associated with comminuted fracture.

Both custom and pre-fabricated splints are employed for the treatment of mallet finger deformity. The custom splint is a padded aluminum flat secured on either anterior or posterior or both anterior and posterior aspect of the finger with bandaging tape. Pre-fabricated splint, also called Stack splint, is available in different sizes and like the custom splint it needs to be secured on the finger with the bandaging tape. Both the existing splinting techniques often result in skin maceration, ulceration, and foul smell due to moisture deposition within the splint, and also restrict patients from getting the finger wet. For hygienic purpose these splints need to be carefully removed and reapplied without flexing the DIP joint. This involves the risk of accidental loss of positioning maintained by the splint. The pre-fabricated splint comes in different sizes yet often finding the correct size is almost impossible.

In view of the foregoing, the drawbacks of the existing custom and pre-fabricated splints may be stated as follows. Firstly, these splints cover maximum skin surface and occlude air for skin breathing, which often results in skin complications. Secondly, these splints include use of hook-and-loop type fastening strips or adhesive tape which absorbs sweat and moisture and so do not allow patients to get the splints wet. Thirdly, the pre-fabricated splints may not be available in the correct size. Lastly, but not the least, these splints give the patient the control to remove and re-apply the splint for hygienic maintenance, which may be detrimental particularly in the acute state and create a risk of delayed healing or non-healing.

Accordingly, there remains a need in the art for a splinting technique that will overcome these drawbacks and the problems that remain unsolved.

SUMMARY OF THE INVENTION

The present invention overcomes the aforementioned deficiencies and the problems that remain unsolved by providing an apparatus, method and system for treating the mallet finger deformity (referred to hereinafter as a flexion deformity) by splinting the DIP joint in a neutral or slight hyperextension position with minimal skin contact. So the splinting technique of the present invention is based on the concept of minimum skin contact (referred to hereinafter as Minimal Contact Splinting or MCS) with the involved body part. The material used by the splinting apparatus, method and system does not absorb moisture, allows the skin to breath in open air, and avoids skin maceration and ulceration. Removal of the splinting apparatus and system is not required for cleaning purposes or for washing the patient's hand. The splinting apparatus and system can be customized to accommodate the shape and size of the finger. It can be easily disassembled and re-assembled with use of a simple tool during a follow-up clinical examination by the physician and during a rehabilitation phase when the splint is used only during night-time hours.

In one aspect of the present invention, a splinting apparatus for treating a flexion deformity of a finger includes:
  a phalangeal bracket;
  a first anchoring ring fixedly attached to the phalangeal bracket and being configured for positioning the phalangeal bracket and respective first anchoring ring proximally of a flexion deformity of a finger;
  a nail bracket;
  a second anchoring ring fixedly attached to the nail bracket and being configured for positioning the nail bracket and respective second anchoring ring distally of the flexion deformity of the finger and closely adjacent to a nail of the finger; and
  a rigid connecting rod extending between, and fixedly attached to at least one of, the phalangeal and nail brackets so as to couple the phalangeal and nail brackets in a spaced apart positional relationship to each other along the finger relative to the flexion deformity of the finger with the phalangeal bracket and respective first anchoring ring being positioned proximally, and the nail bracket and respective second anchoring ring being positioned distally, of the flexion deformity of the finger;
  wherein the first and second anchoring rings are respective bands configured for being extendible circumferentially about the finger at respective positions proximally and distally of the flexion deformity of the finger such that the phalangeal and nail brackets and the respective first and second anchoring ring bands therewith are secured in the spaced apart positional relationship respectively proximally and distally of the flexion deformity of the finger, the nail bracket and an adjacent portion of the respective second anchoring ring band are maintained closely adjacent to the top surface of the finger nail for adhering the nail bracket and the adjacent portion of the respective second anchoring ring band to a top surface of the finger nail, the connecting rod extends over the flexion deformity of the finger in a spaced relationship thereto, and the finger is maintained in a substantially neutral or slight hyperextension position.

In another aspect of the present invention, a splinting method for treating a flexion deformity of a finger includes:
  obtaining a first anchoring ring fixedly attached to a phalangeal bracket;

obtaining a second anchoring ring fixedly attached to a nail bracket;

positioning the phalangeal bracket and first anchoring ring proximally of a flexion deformity of a finger by bending first and second band extensions of the first anchoring ring in opposite directions circumferentially about the finger proximally of the flexion deformity of the finger and securing overlapping free end portions of the first and second band extensions to one another so as to secure the first anchoring ring about the finger;

positioning the nail bracket and second anchoring ring distally of the flexion deformity of the finger and closely adjacent to a nail of the finger by bending first and second band extensions of the second anchoring ring in opposite directions circumferentially about the finger at the location of the finger nail and distally of the flexion deformity of the finger and securing overlapping free end portions of the first and second band extensions to one another so as to secure the second anchoring ring about the finger;

adhesively securing the nail bracket and an adjacent portion of the respective second anchoring ring to a top surface of the finger nail; and positioning a rigid connecting rod between, and fixedly attaching the connecting rod to at least one of, the phalangeal and nail brackets so as to couple the phalangeal and nail brackets and the respective first and second anchoring rings therewith in a spaced apart positional relationship to each other respectively proximally and distally of the flexion deformity of the finger, dispose the connecting rod over the flexion deformity of the finger in a spaced relationship thereto, and maintain the finger in a substantially neutral or slight hyperextension position.

In still another aspect of the present invention, a splinting system for treating a flexion deformity of a finger includes:

a phalangeal bracket comprising a pair of opposed side tabs each having an aperture defined therethrough such that the apertures are aligned with one another;

a first anchoring ring fixedly attached to the phalangeal bracket and being configured for positioning the phalangeal bracket and first anchoring ring proximally of a flexion deformity of a finger, the first anchoring ring comprising first and second band extensions rigidly attached to one another and to the opposed side tabs of the phalangeal bracket, the first and second band extensions extending in opposite directions from the phalangeal bracket and terminating in respective free end portions, the first and second band extensions being bendable in opposite directions circumferentially around the finger, the free end portion of one of the band extensions having a pair of wings thereon protruding in opposite directions from opposite longitudinal edges of said one band extension and configured to bend in opposite directions around opposite longitudinal edges of the other of the band extensions so as to secure the band extensions circumferentially around the finger, proximally of the flexion deformity of the finger, with the free end portions of the band extensions in an overlapping relationship to one another;

a nail bracket comprising a pair of opposed side tabs each having an aperture defined therethrough such that the apertures are aligned with one another;

a second anchoring ring fixedly attached to the nail bracket and being configured for positioning the nail bracket and second anchoring ring distally of the flexion deformity of the finger and closely adjacent to a nail of the finger, the second anchoring ring comprising first and second band extensions rigidly attached to one another and to the opposed side tabs of the nail bracket, the first and second band extensions extending in opposite directions from the nail bracket and terminating in respective free end portions, the first and second band extensions being bendable in opposite directions circumferentially around the finger, the free end portion of one of the band extensions having a pair of wings thereon protruding in opposite directions from opposite longitudinal edges of the one band extension and configured to bend in opposite directions around opposite longitudinal edges of the other of the band extensions so as to secure the band extensions circumferentially around the finger, distally of the flexion deformity of the finger, with the free end portions of the band extensions in an overlapping relationship to one another; and a rigid connecting rod extending between, and fixedly attached to at least one of, the phalangeal and nail brackets, the connecting rod at respective opposite end portions thereof being received through the aligned apertures of the opposed side tabs of the phalangeal bracket and of the nail bracket so as to couple the phalangeal and nail brackets in a spaced apart positional relationship to each other along the finger relative to the flexion deformity of the finger with the phalangeal bracket and respective first anchoring ring being positioned proximally, and the nail bracket and respective second anchoring ring being positioned distally, of the flexion deformity of the finger;

wherein the nail bracket and an adjacent portion of the respective second anchoring ring are maintained closely adjacent to the top surface of the finger nail for adhering the nail bracket and the adjacent portion of the respective second anchoring ring to the top surface of the finger nail, the connecting rod extends over the flexion deformity of the finger in a spaced relationship thereto, and the finger is maintained in a substantially neutral or slight hyperextension position.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

Figure 1:
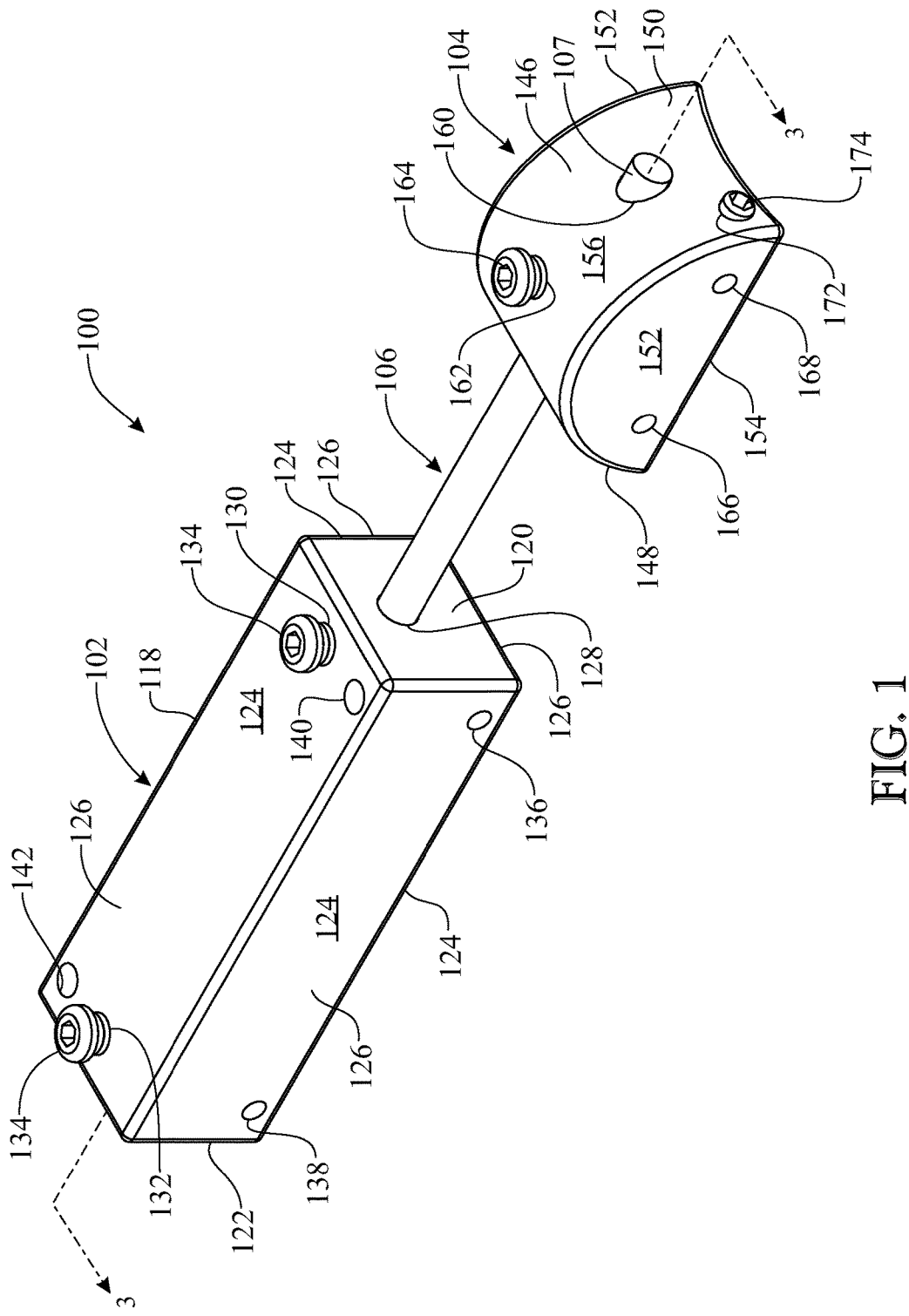
FIG. 1 presents an upper isometric assembled view of a first implementation of a splinting apparatus and system for treating a flexion deformity of a finger in accordance with one aspect of the present invention, the view showing a connecting rod of the apparatus and system assembled to phalangeal and nail brackets of the apparatus and system but not showing an anchoring wire of the apparatus and system that is employed in attaching the splinting apparatus and system to the finger with the particular deformity.
Figure 2:
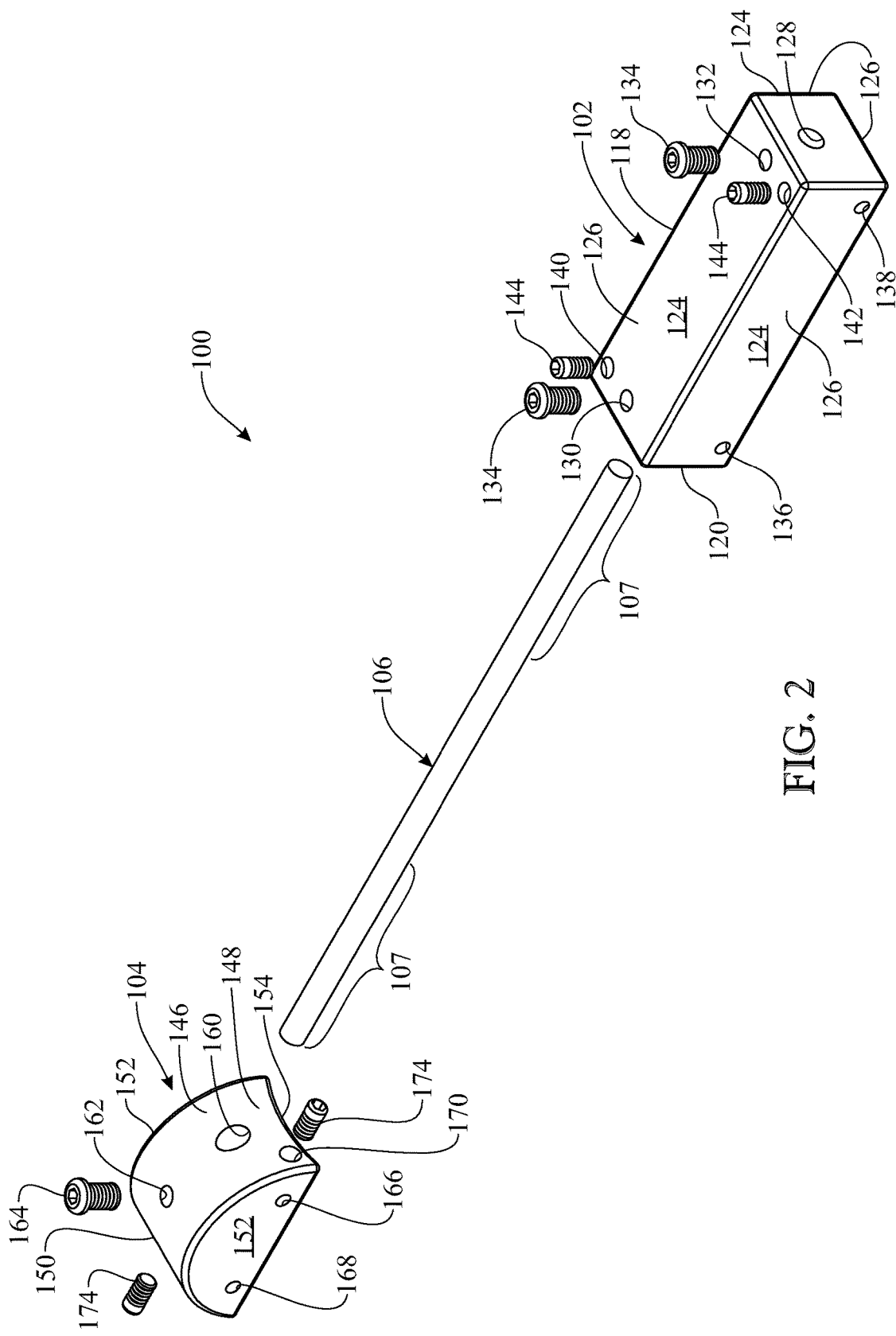
FIG. 2 presents an upper isometric exploded view of the connecting rod and phalangeal and nail brackets of the splinting apparatus and system of FIG. 1.
Figure 3:
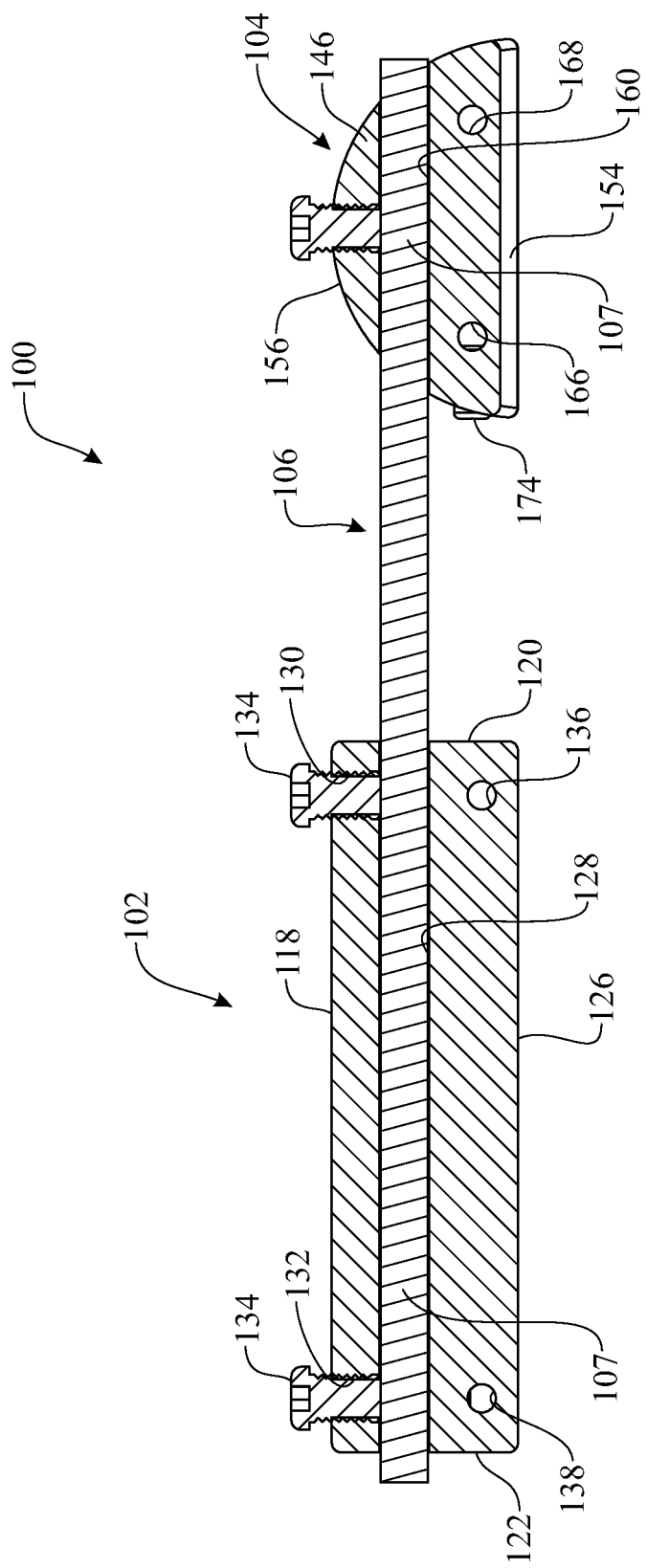
FIG. 3 presents a longitudinal sectional view of the connecting rod and phalangeal and nail brackets of the splinting apparatus and system taken along line 3-3 of FIG. 1.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Referring now to FIGS. 1-6, there is illustrated a first implementation of a splinting apparatus (and system), generally designated 100, for treating a flexion deformity of a finger in accordance with an aspect of the present invention. As seen in FIGS. 1-6, the apparatus 100 includes a phalangeal bracket 102, a nail bracket 104 and a connecting rod 106. As further seen in FIGS. 4-6, the apparatus 10 also includes an anchoring wire 108.

Figure 4:
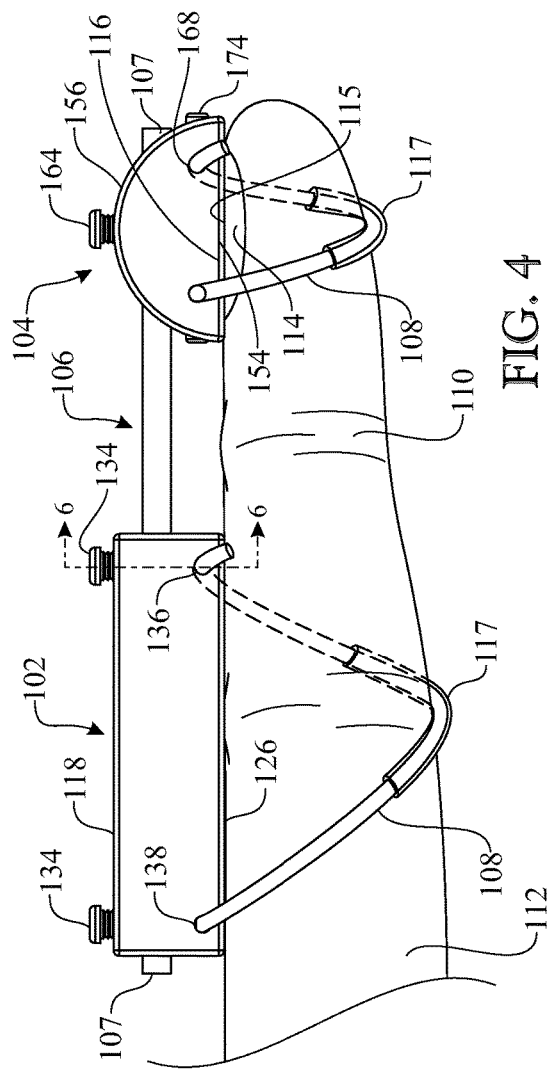
FIG. 4 presents a side elevation view of the splinting apparatus and system in accordance with another aspect of the present invention, the view showing separate anchoring wires circumferentially attaching the brackets to a finger, with portions of the separate wires being padded.
Figure 5:
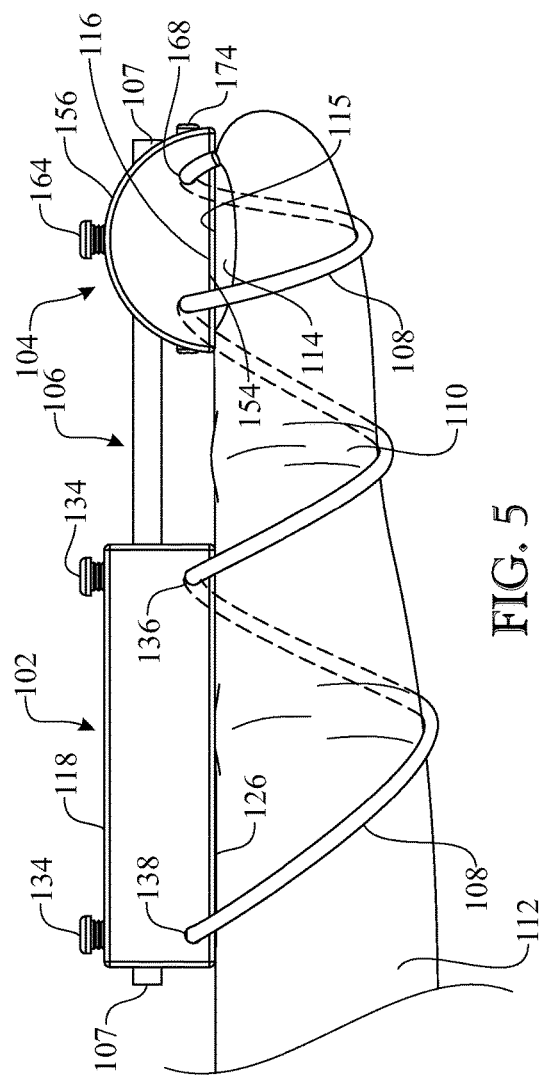
FIG. 5 presents a side elevation view of the splinting apparatus and system in accordance with still another aspect of the present invention, the view showing a common or continuous unpadded anchoring wire circumferentially attaching the brackets to the finger.

As shown in FIGS. 4 and 5, the phalangeal bracket 102 is configured for positioning proximally of a flexion deformity 110 of a finger 112 in contact with the skin 113 of the finger 112. The nail bracket 104 is configured for positioning distally of the flexion deformity 110 of the finger 112 closely adjacent to a top surface 115 of a nail 114 of the finger 112 in contact with a layer 116 of a suitable adhesive, such as a glue, resin or a similar substance, on the top surface 115 of the nail 114 so as to adhere the nail bracket 104 to the top surface 115 of the nail 114.

The connecting rod 106 is made of a material of a suitable diameter and being substantially rigid such as steel rod material. The rod 106 extends between and is fixedly attached to the phalangeal bracket 102 (in the manner as best seen in FIG. 6 and explained hereinafter) and substantially similarly to the nail bracket 104 so as to provide the brackets 102, 104 in a fixed spaced apart positional relationship to each other.

Figure 6:
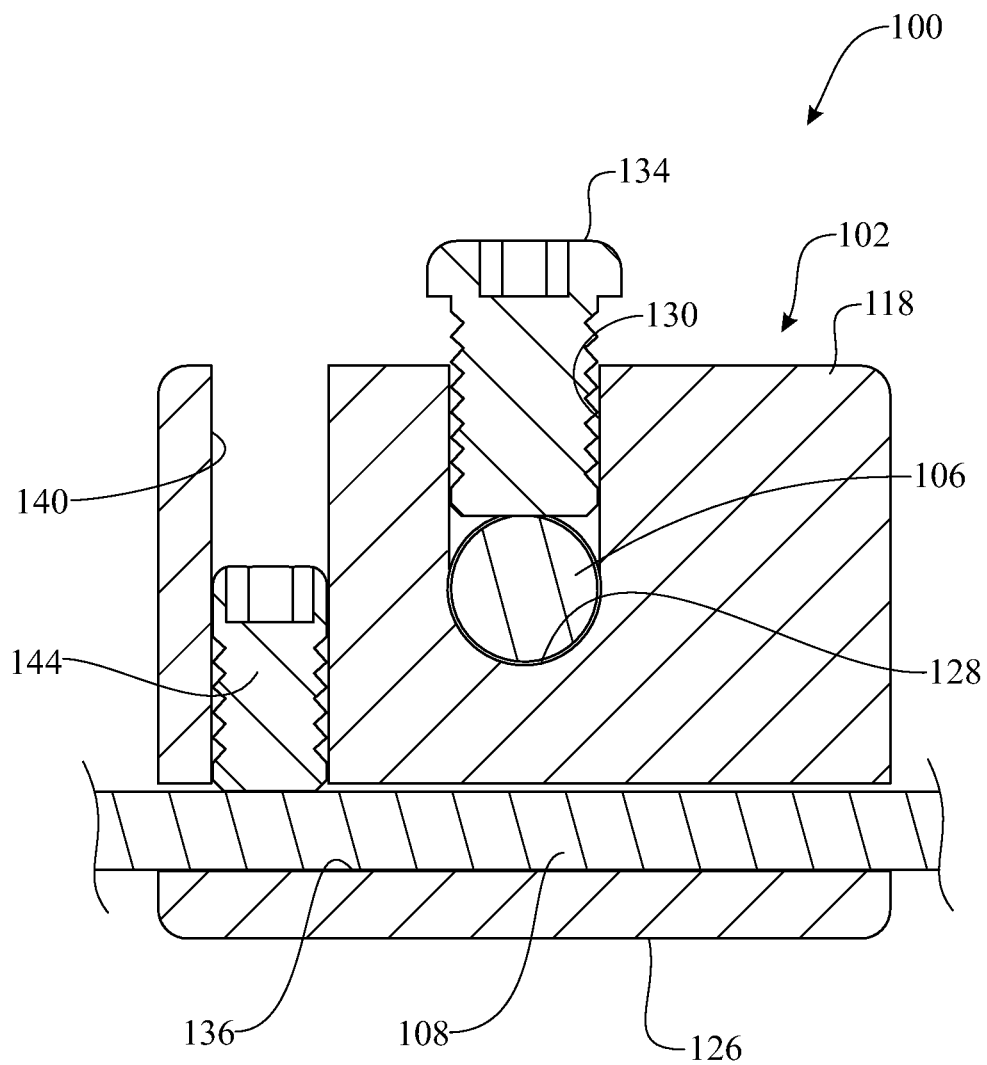
FIG. 6 presents an enlarged cross-sectional view of the phalangeal bracket of the splinting apparatus and system taken along line 6-6 of FIG. 4, the view showing portions of the connecting rod and anchoring wire.

The anchoring wire 108 is fixedly attached to the phalangeal bracket 102 (in the manner also as best seen in FIG. 6 and explained hereinafter) and substantially similarly to the nail bracket 104. The anchoring wire 108 is made of a material being substantially stiff but bendable, such as steel wire being 1 mm in diameter, so that the wire 108 can be configured by bending it into the desired curvature, for example by using a suitable tool such as curve-making pliers, to extend the wire 108 circumferentially about the finger 112 such that the phalangeal and nail brackets 102, 104 may be secured in a fixed positional relationship to the finger 112.

In such positional relationship, the phalangeal bracket 102 is maintained in minimal skin contact with the finger 112, the nail bracket 104 is maintained closely adjacent and adhered to the top surface 115 of the nail 114 of the finger 112, the connecting rod 106 extends over the flexion deformity 110 of the DIP joint of the finger 112 in a spaced relationship thereto, and the finger 112 is maintained in a substantially neutral or slight hyperextension position, as seen in FIGS. 4 and 5. Also, the anchoring wire 108 may be at least partially padded by placement of a tubing 117, such as catheter tubing made of a suitable flexible plastic material, over the wire 108 and along portions thereof that contact the skin 113 of the DIP joint of the finger 112. Also, the anchoring wire 108 may be either interrupted, or in two different lengths, so as to not extend between the phalangeal and nail brackets 102, 104, as seen in FIG. 4, or continuous, or in a single length, so as to extend between the brackets 102, 104, as seen in FIG. 5, and provide extra stability.

More particularly, as shown in FIGS. 1-6 and 11, the phalangeal bracket 102 has a body 118 that, in this first implementation of the apparatus 100, is rectangular shaped. The body 118 has a pair of opposite end portions 120, 122, a plurality of side portions 124, and an exterior surface 126 on the side portions 124 extending lengthwise of the body 118 between the opposite end portions 120, 122. The exterior surface 126 is configured to made contact with the skin 113 of the finger 112 proximally of the flexion deformity 110.

Referring still to FIGS. 1-6 and 11, the body 118 of phalangeal bracket 102 further has a bore 128 and a pair of threaded holes 130, 132. The bore 128 is substantially straight and cylindrical in configuration. The bore 128 extends lengthwise of, and interiorly through, the body 118 and is open at least at one and preferably both of the opposite end portions 120, 122 of the body 118. The bore 128 may be formed by drilling it longitudinally, or lengthwise, through the body 118 to provide it with a suitable diameter slightly greater than the diameter of the connecting rod 106. The connecting rod 106 at a respective one of a pair of opposite end portions 107 thereof, as seen in FIGS. 1 and 3-5, is received within the bore 128. The threaded holes 130, 132 are tapped adjacent to the opposite end portions 120, 122 of the body 118 so as to extend between, and be open at, the exterior surface 126 of the body 118 and the bore 128 through the body 118.

The apparatus 100 also includes set screws 134 threadably inserted into the threaded holes 130, 132 from the exterior surface 126 of the body 118 into the bore 128 through the body 118. In such manner, the set screws 134 contact and hold the connecting rod 106 in a fixedly attached relationship in the body 118 thereby securing the connecting rod 106 in the fixed positional relationship with the phalangeal bracket 102.

The body 118 of the phalangeal bracket 102 still further has a pair of passageways 136, 138 and a pair of threaded holes 140, 142. Each of the passageways 136, 138 extends transversely or crosswise of, and interiorly through, the body 118 and is open at an opposite pair of the side portions 124 of the body 118 at a respective one of the opposite end portions 120, 122 of the body 118. The passageways 136, 138 may be formed by drilling them crosswise through the body 118 to provide them with a suitable diameter slightly greater than the diameter of the anchoring wire 108. Each of the threaded holes 140, 142 is tapped into the body 118 so as to extend between, and be open at, the exterior surface 126 of the body 118 and a respective one of the passageways 136, 138 through the body 118. Further, the threaded holes 140 are located at a respective one of a pair of opposite ends of the corresponding passageways 136, 138 that at opposite ones of the side portions 152 of the body 118.

The apparatus 100 also includes set screws 144 threadably inserted into the threaded holes 140, 142 from the exterior surface 126 of the body 118 into the respective passageways 136, 138 through the body 118 so as to contact and hold the anchoring wire 108 in a fixedly attached relationship in the body 118 thereby securing the body 118 of the phalangeal bracket 102 in the fixed positional, and a minimal contacting, relationship with the skin 113 of the finger 112. Except for the bore 128 and passageways 136, 138, the body 118 of the phalangeal bracket 102, through which the bore 128 and passageways 136, 138 are formed, is made of a solid material, such as (but not so limited to) a metal or plastic material. By way of example but not of limitation, the phalangeal bracket 102, having the rectangular shaped body 118, may be 15 mm in length, 5 mm in width and 5 mm in height. As stated before, the body 118 can be of any suitable shape, with smooth edges.

Referring now to FIGS. 1-5 and 9, the nail bracket 104 of the apparatus 100 has a body 146, which can be any suitable shape with smooth edges, by way of example but not limitation, such as semi-cylindrical shaped. The body 146 has a pair of opposite end portions 148, 150, a plurality of side portions 152, and at least two exterior surfaces 154, 156 extending lengthwise between the opposite end portions 148, 150. One exterior surface 154 is configured to accommodate positioning it closely adjacent to the top surface 115 of the nail 114 of the finger 112 for adhering it to the top surface 115. Since the top surface 115 of the finger nail 114 typically is curved in configuration, the one exterior, or bottom, surface 154 of the nail bracket 104 is similarly curved in configuration and also roughened by incorporation of corrugations 158 thereon so as to facilitate adhering of the nail bracket 104 to the top surface 115 of the finger nail 114, such as with the layer 116 of adhesive disposed between the one exterior surface 154 of the nail bracket 104 and the top surface 115 of the finger nail 114.

The body 146 of the nail bracket 104 further has a bore 160 and a threaded hole 162. The bore 160 is substantially straight and cylindrical in configuration. The bore 160 extends lengthwise of, and interiorly through, the body 146 and is open at least at one and preferably both opposite end portions 148, 150 of the body 146. The bore 160 may be formed by drilling it longitudinally, or lengthwise, through the body 146 to provide it with a suitable diameter slightly greater than the diameter of the connecting rod 106. The connecting rod 106 at a respective one of the opposite end portions 107 thereof, as seen in FIGS. 1 and 3-5, is received within the bore 160. The threaded hole 162 is tapped in the other exterior surface 156 midway between the opposite end portions 148, 150 of the body 146 so as to extend between, and be open at, the other exterior surface 156 of the body 146 and the bore 160 through the body 146.

The apparatus 100 also includes a set screw 164 threadably inserted into the threaded hole 162 from the other exterior surface 156 of the body 146 into the bore 160 through the body 146. In such manner, the set screw 164 contacts and holds the connecting rod 106 in a fixedly attached relationship in the body 146 thereby securing the connecting rod 106 in the fixed positional relationship with the nail bracket 104.

The body 146 of the nail bracket 104 still further has a pair of passageways 166, 168 and a pair of threaded holes 170, 172. Each of the passageways 166, 168 extends transversely or crosswise of, and interiorly through, the body 146 and is open at least at an opposite pair of the side portions 152 of the body 146. The passageways 166, 168 may be formed by drilling them crosswise through the body 146 to provide them with a suitable diameter slightly greater than the diameter of the anchoring wire 108. Each of the threaded holes 170, 172 is tapped into the body 146 so as to extend between, and be open at, the other exterior surface 156 of the body 146 and a respective one of the passageways 170, 172 through the body 146. Further, the threaded holes 170, 172 are located at a respective one of a pair of opposite ends of the corresponding passageways 166, 168 at opposite ones of the side portions 152 of the body 146.

The apparatus 100 also includes set screws 174 threadably inserted into the threaded holes 170, 172 from the other exterior surface 156 of the body 146 into the respective passageways 166, 168 through the body 146 so as to contact and hold the anchoring wire 108 in a fixedly attached relationship in the body 146 thereby securing the body 146 of the nail bracket 104 in the fixed positional relationship with the nail 114 of the finger 112 closely adjacent to the top surface 115 of the nail 114 for adhering the nail bracket 104 to the top surface 115 of the nail 114. Like the body 118 of the phalangeal bracket 102, the body 146 of the nail bracket 104 is made of a solid material, such as (but not so limited to) a metal or plastic material. By way of example but not of limitation, the nail bracket 014 may be 8 mm in length, 5 mm in width, and 5 mm in height. The body 146 may be of any suitable shape, with smooth edges.

Figure 7:
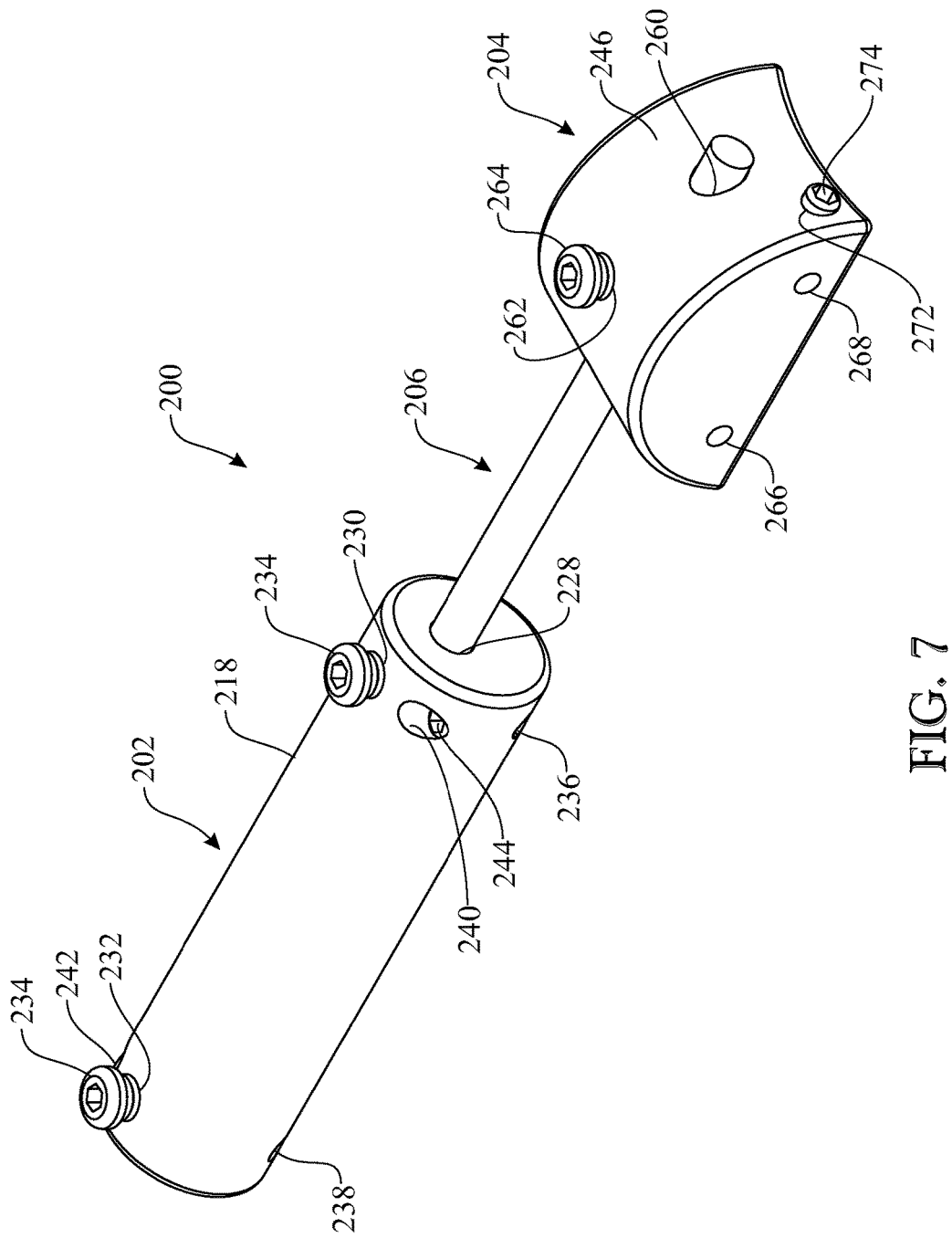
FIG. 7 presents an upper isometric assembled view of a second implementation of the splinting apparatus and system for treating a flexion deformity of a finger in accordance with a further aspect of the present invention, the view showing a phalangeal bracket generally cylindrical shaped instead of the generally rectangular shaped phalangeal bracket of FIGS. 1-6.
Figure 8:
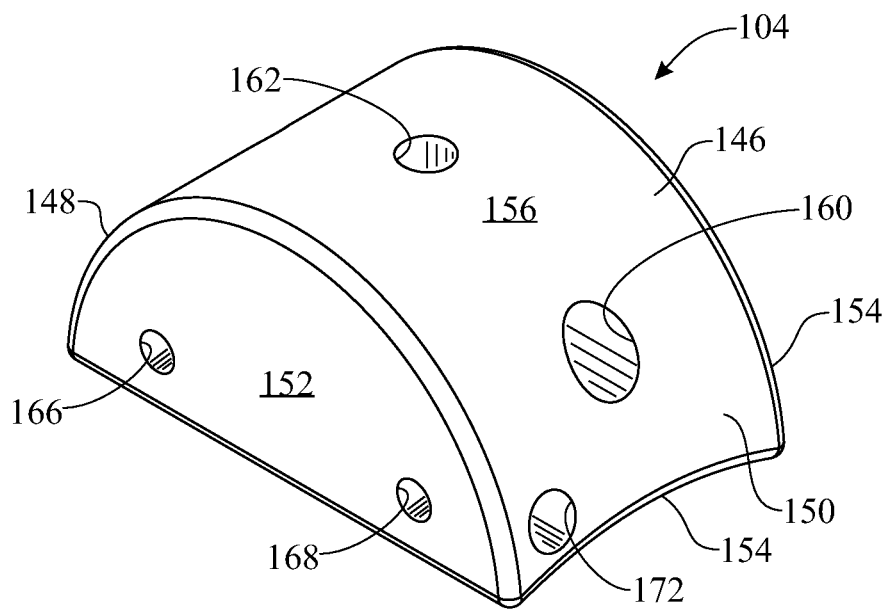
FIG. 8 presents an enlarged upper isometric view of the nail bracket of the splinting apparatus and system.
Figure 9:
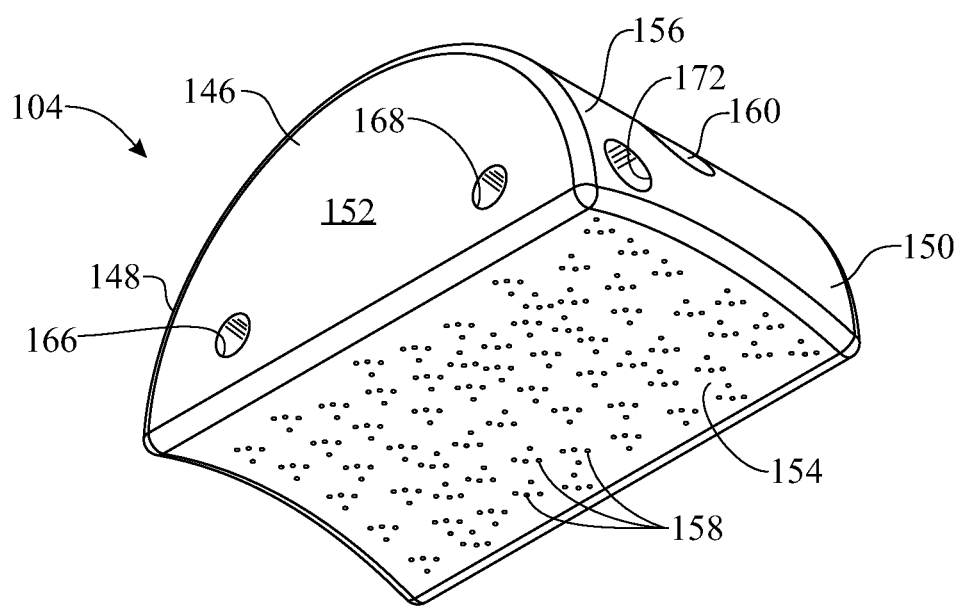
FIG. 9 presents an enlarged lower isometric view of the nail bracket of the splinting apparatus and system, the view showing a corrugated bottom surface to aid in adhering the nail bracket to a top surface of a nail.
Figure 10:
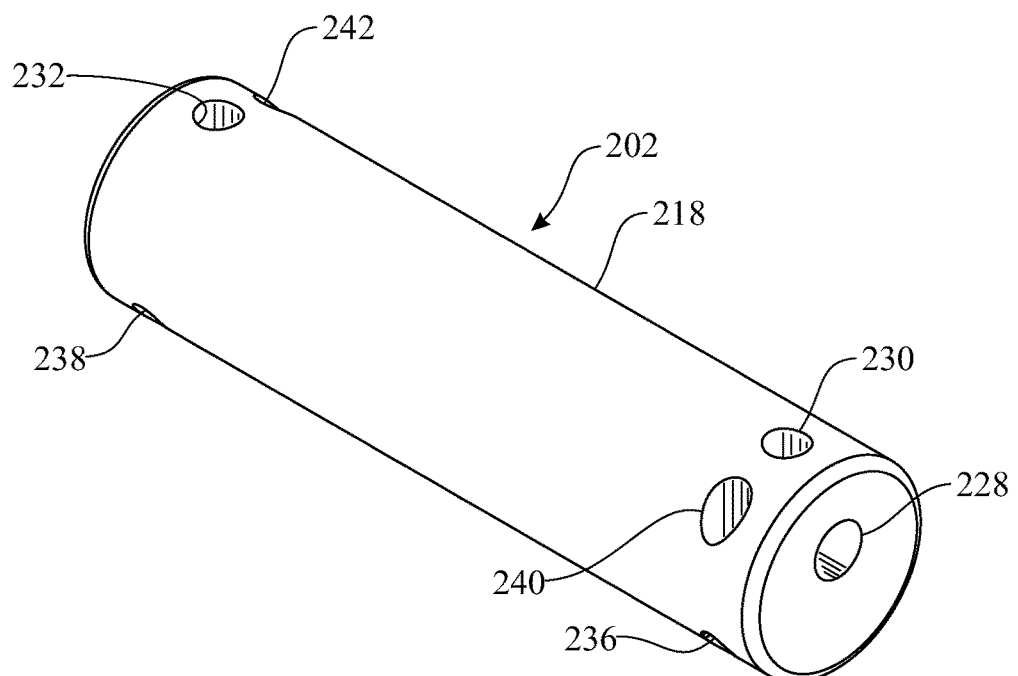
FIG. 10 presents an enlarged upper isometric view of the phalangeal bracket of the splinting apparatus and system of FIG. 7.
Figure 11:
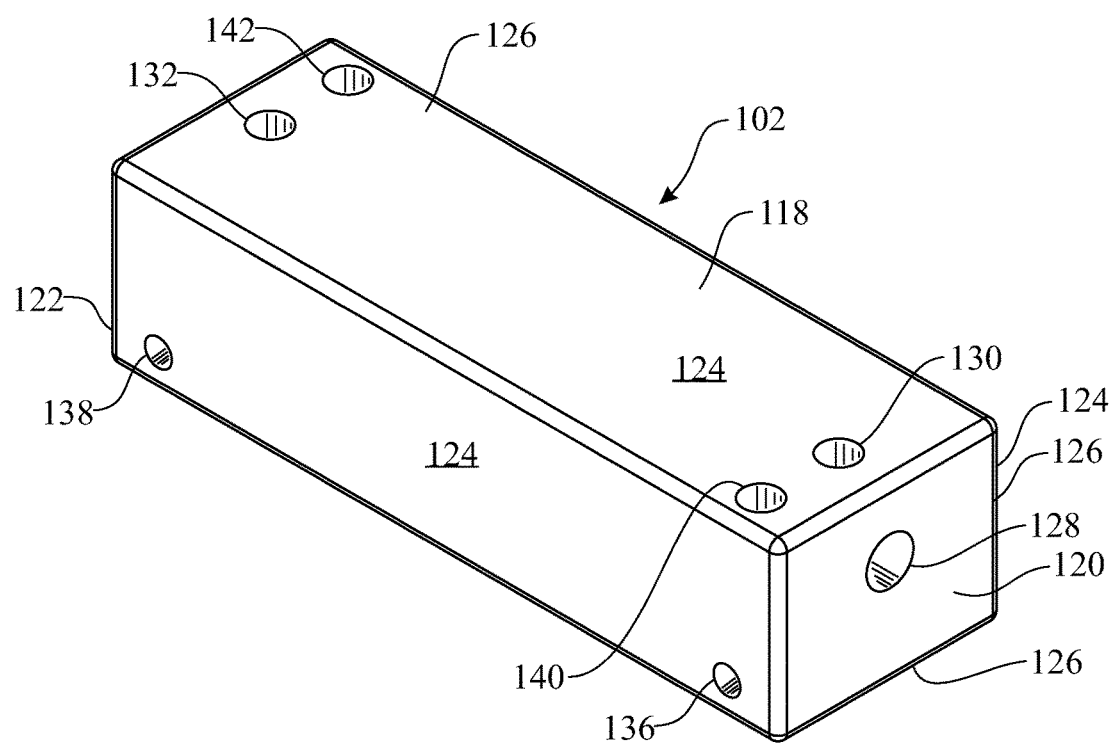
FIG. 11 presents an enlarged upper isometric view of the phalangeal bracket of the splinting apparatus and system of FIGS. 1-6.

Referring now to FIGS. 7 and 10, there is illustrated a second implementation of a splinting apparatus, generally designated 200, for treating a flexion deformity of a finger in accordance with an aspect of the present invention. Features of the apparatus 200 of the second implementation which are specifically mentioned hereinafter are some (but not all) of the features substantially like those of the apparatus 100 of the first implementation. Like features are numbered the same except preceded by the numeral '2'. These features of the apparatus 200 include a phalangeal bracket 202, a nail bracket 204, and a connecting rod 206. These features also include the following ones associated with the phalangeal bracket 202: a body 218, a bore 228 lengthwise through body 218, threaded holes 230, 232 opening into the bore 218, passageways 236, 238 crosswise through the body 218, threaded holes 240, 242 opening into passageways 236, 238, set screws 234 inserted in the threaded holes 230, 232 and a set screw 244 inserted in the threaded hole 240. These features further include the following ones associated with the nail bracket 204: a body 246, a bore 260 lengthwise through the body 246, a threaded hole 262 opening into the bore 260, set screw 264 passageways 266, 268 crosswise through the body 246, a threaded hole 272 opening into the passageway 268, and a set screw 274 inserted into the threaded hole 272. It will be readily apparent that the primary difference of the apparatus 200 from the apparatus 100 is the cylindrical shape of the body 218 of the phalangeal bracket 202. The phalangeal bracket 102, 202 may be other shapes as well.

Figure 12:
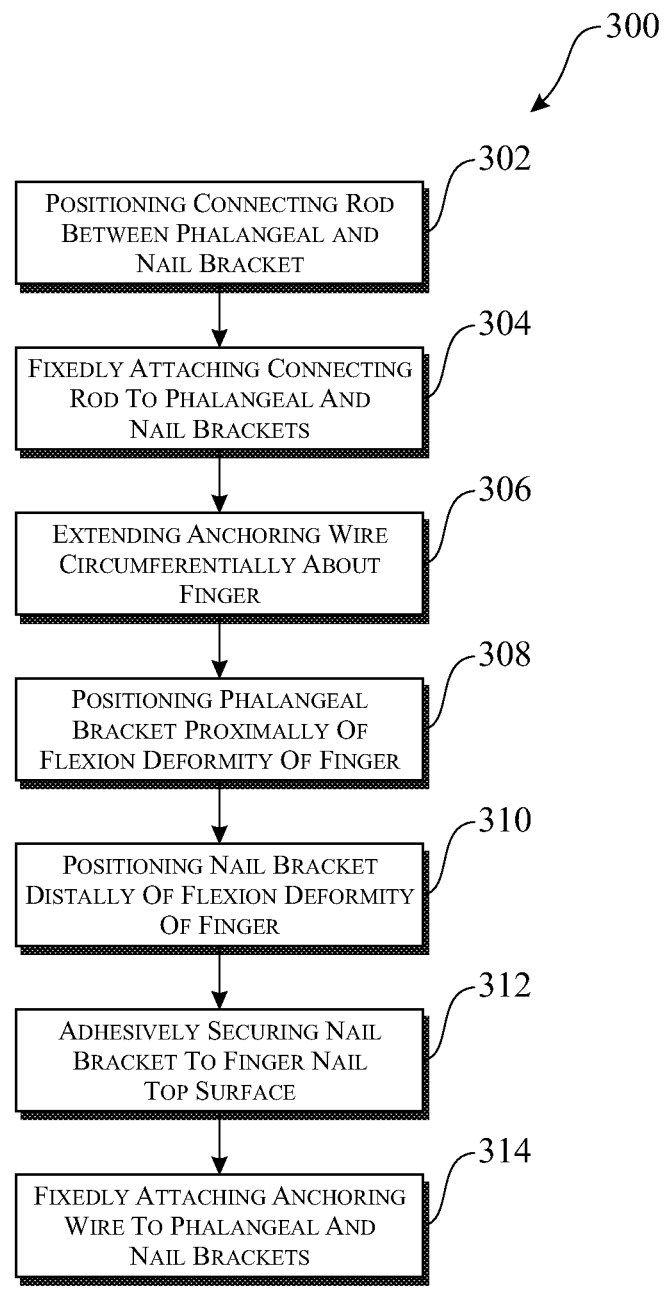
FIG. 12 presents a flow diagram of a first exemplary embodiment of a splinting method for treating a flexion deformity of a finger using either of the first and second implementations of the splinting apparatus and system in accordance with still another aspect of the present invention.

Referring now to FIG. 12, there is illustrated a flow chart, generally designated 300, showing in diagrammatical form a plurality of steps, which will now be briefly described with reference to the first implementation of the apparatus 100, that make up a splinting method, according to another aspect of the present invention, for treating the flexion deformity 110 of the finger 112. It should be understood that the steps of the method may occur in a different order with respect to each other than as described hereinafter.

Block 302 of the flow chart 300 represents the step of positioning the rigid connecting rod 106 between phalangeal and nail brackets 102, 104. Block 304 of flow chart 300 represents the step of fixedly attaching opposite end portions 107 of the rigid connecting rod 106 to the phalangeal and nail brackets 102, 104 so as to provide the brackets 102, 104 in a fixed spaced apart positional relationship to each other that will position the brackets 102, 104 in the desired positions along the finger 112 relative to the flexion deformity 110 of the finger 112. Block 306 of flow chart 300 represents the step of extending the anchoring wire 108 circumferentially about the finger 112 both proximally and distally of the flexion deformity 110 of the finger 112.

Block 308 of the flow chart 300 represents positioning the phalangeal bracket 102 proximally of the flexion deformity 110 of the finger 112. Block 310 of flow chart 300 represents the step of positioning the nail bracket 104 distally of the flexion deformity 110 of the finger 112. Block 312 of flow chart 300 represents adhesively securing the nail bracket 104 to the top surface 115 of the nail 114 of the finger 112. Block 314 of flow chart 300 represents the step of fixedly attaching the anchoring wire 108 to the phalangeal and nail brackets 102, 104 such that the brackets 102, 104 are secured in a fixed positional relationship to the finger 112, the phalangeal bracket 102 is maintained in minimal skin contact with the finger 112, the nail bracket 104 is maintained adhered to the top surface 115 of the finger nail 114, the connecting rod 106 bridges the flexion deformity 110 of the finger 112 in a spaced relationship thereto, and the DIP joint of the finger 112 is maintained in a substantially neutral or slight hyperextension position.

Figure 13:
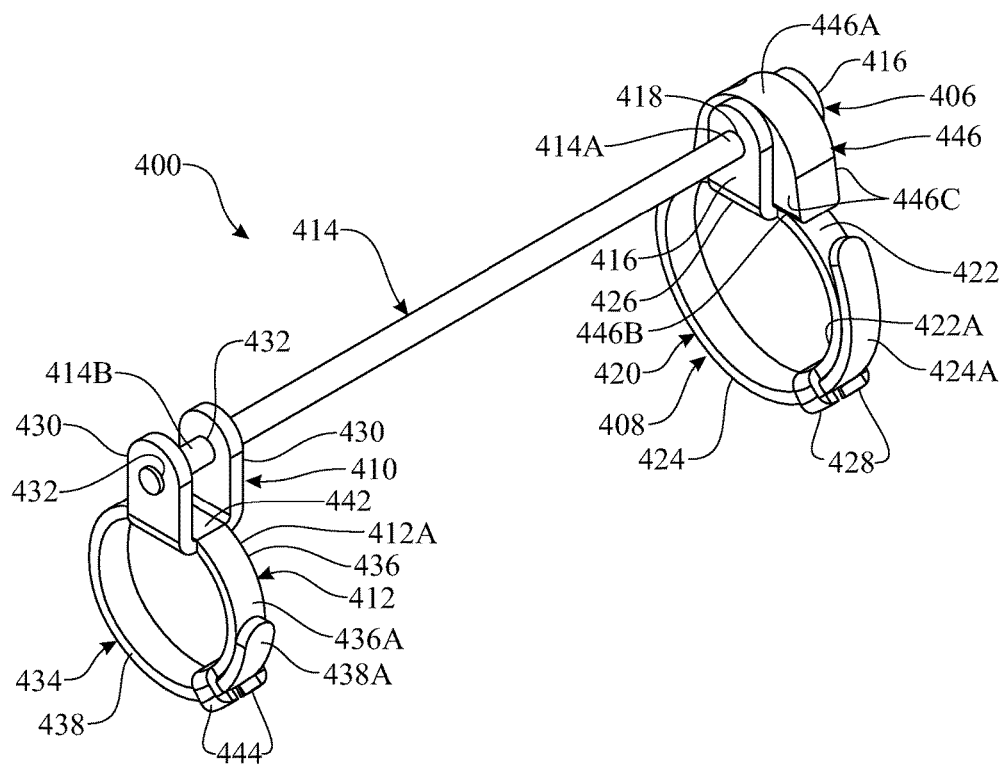
FIG. 13 presents an upper isometric assembled view of a third implementation of the splinting apparatus and system for treating a flexion deformity of a finger in accordance with a further aspect of the present invention, the view showing a connecting rod assembled to nail and phalangeal brackets being affixed respectively on anchoring rings employed in attaching the splinting apparatus and system to the finger with the particular deformity.

Referring now to FIGS. 13-18, there is illustrated a third implementation of a splinting apparatus (and system), generally designated 400, for treating a flexion deformity 402 of a finger 404 in accordance with an aspect of the present invention. As seen in FIG. 13, the apparatus 400 includes a phalangeal bracket 406, a first anchoring ring 408, a nail bracket 410, a second anchoring ring 412, and a rigid connecting rod 414.

As shown in FIGS. 13, 15, 17 and 18, the phalangeal bracket 406 is in the form of a pair of opposed side tabs 416. Each side tab 416 has an aperture 418 defined therethrough such that the apertures 418 are aligned with one another. The first anchoring ring 408 is in the form of a strap or band 420 having first and second band extensions 422, 424 fixedly attached to the phalangeal bracket 406. The first anchoring ring 408 is configured to position the phalangeal bracket 406 and first anchoring ring 408 proximally of the flexion deformity 402 of the finger 404. Also, the phalangeal bracket 406 and the band 420 of the first anchoring ring 408 share a bight 426 being an integral part of both of them or where they are integrally connected together. The bight 426 is rigidly attached to, and extends between, lower ends of the opposed side tabs 416 such that the phalangeal bracket 406 has a substantially rigid U-shaped configuration. The bight 426 is also fixedly or integrally attached to, and extends between, adjacent ends of the first and second band extensions 422, 424 of the band 420 with the latter extending in opposite directions therefrom, terminating in respective free end portions 422A, 424A. The first band extension 422 may be shorter in length than the second band extension 424.

Figure 15:
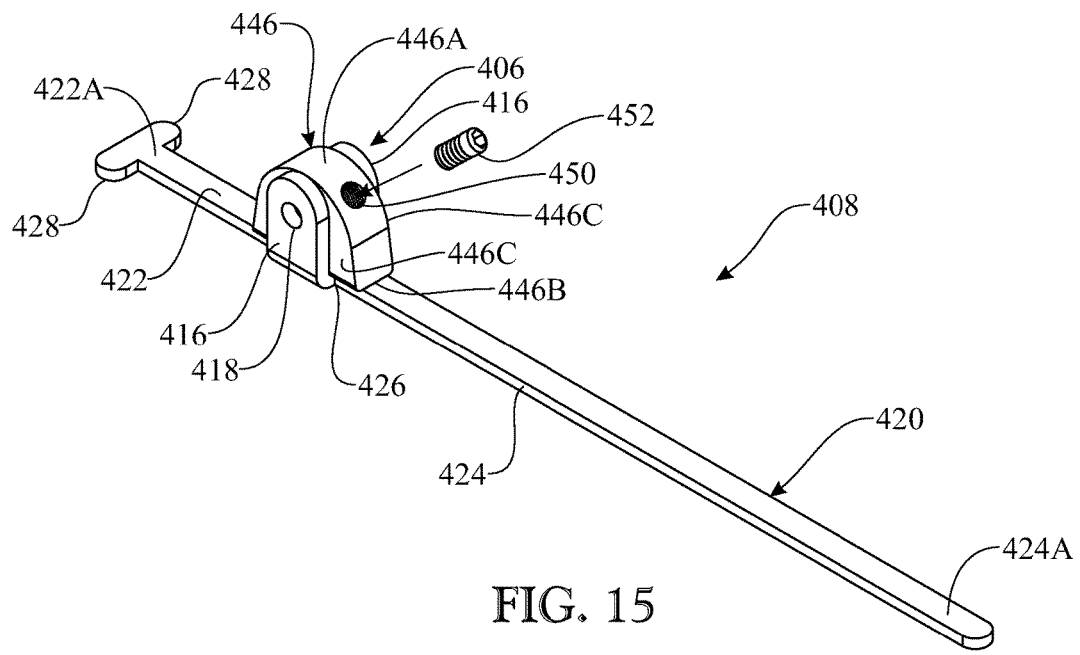
FIG. 15 presents an upper isometric view of the phalangeal bracket and a pair of band extensions affixed thereto, the band extensions being shown in an initial blank configuration.
Figure 17:
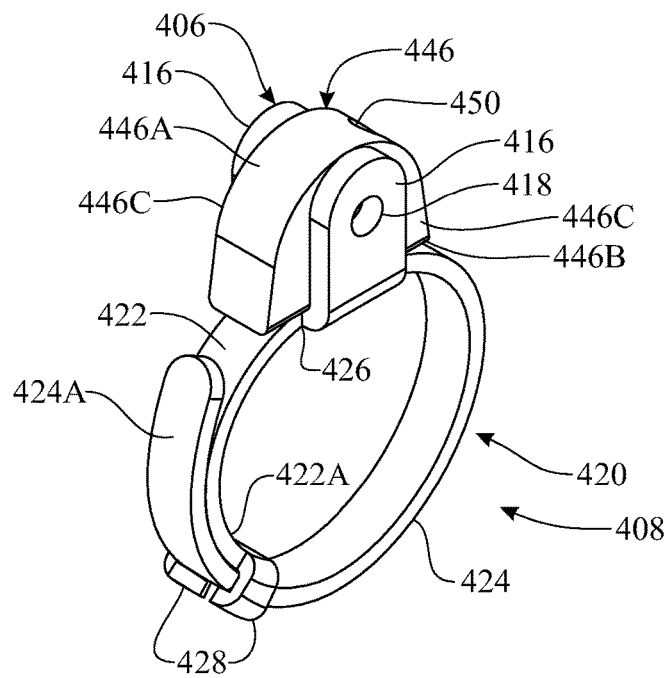
FIG. 17 presents an upper isometric view of the phalangael bracket with the band extensions affixed thereto being shown in a final configuration in the other of the anchoring rings.

In FIG. 15 the first and second band extensions 422, 424 of the band 420 are in an initial configuration in which they have a blank-type form, whereas in FIG. 17 the first and second band extensions 422, 424 of the band 420 now are in a final configuration in which they have been transformed into the form of the first anchoring ring 408. This transformation is accomplished by bending the first and second band extensions 422, 424 of the band 420 in opposite directions circumferentially around the finger 404 such that their respective free end portions 422A, 424A are brought together in an overlapping relationship with respect to one another. The free end portion 422A of the first band extension 422 has a pair of wings 428 formed thereon so as to protrude in opposite directions from opposite longitudinal edges of the first band extension 422. The wings 428 are configured to bend, such as by being crimped, in opposite directions around opposite longitudinal edges of the second band extension 424 so as to secure the band extensions 422, 424 to one another and circumferentially around the finger 404 proximally of the flexion deformity 402 of the finger 404 with the opposite free end portions 422A, 424A in the overlapped relationship. The phalangeal bracket 406 and first anchoring ring 408 may be made from any suitable bendable or pliable material, for example a metal or plastic.

As shown in FIGS. 13, 15, 17 and 18, the nail bracket 410 and the second anchoring ring 412 have substantially the same makeup and configuration as just described in the case of the phalangeal bracket 406 and first anchoring ring 408. In other words, the nail bracket 410 is in the form of a pair of opposed side tabs 430. Each side tab 430 has an aperture 432 defined therethrough such that the apertures 432 are aligned with one another. The second anchoring ring 412 is in the form of a strap or band 434 having first and second band extensions 436, 438 fixedly attached to the nail bracket 410. The second anchoring ring 412 is configured to position the nail bracket 410 and second anchoring ring 412 distally of the flexion deformity 402 of the finger 404 and closely adjacent to a nail 440 of the finger 404. Also, the nail bracket 410 and the band 434 of the second anchoring ring 412 share a bight 442 being an integral part of both of them or where they are integrally connected together. The bight 442 is rigidly attached to, and extends between, lower ends of the opposed side tabs 430 such that the nail bracket 410 has a substantially rigid U-shaped configuration. The bight 442 is also fixedly or integrally attached to, and extends between, adjacent ends of the first and second band extensions 436, 438 of the band 434 with the latter extending in opposite directions therefrom, terminating in respective free end portions 436A, 438A. The first band extension 436 may be shorter in length than the second band extension 438.

Figure 14:
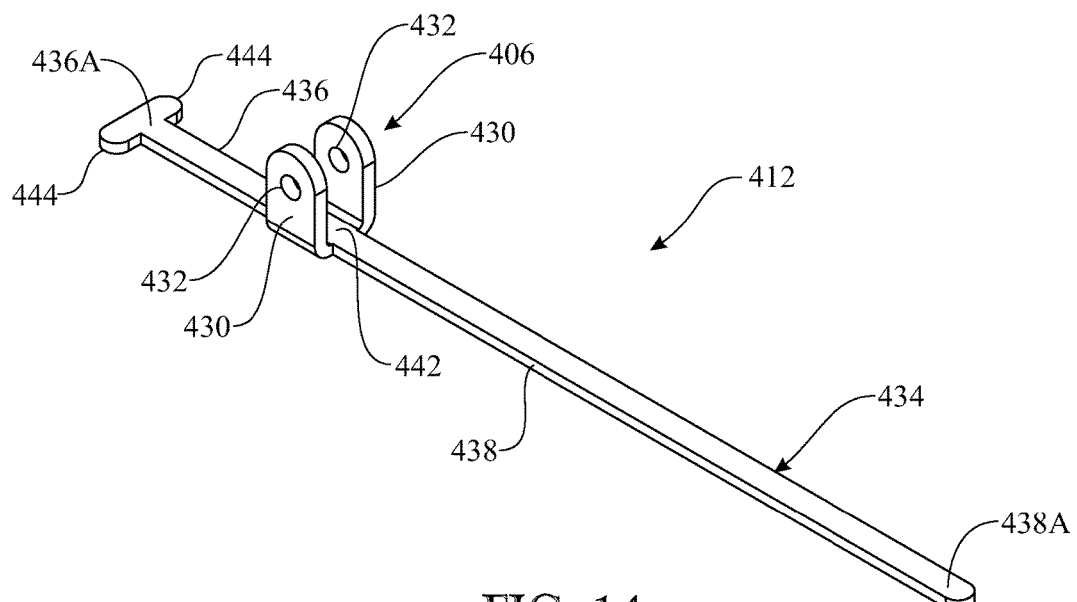
FIG. 14 presents an upper isometric view of the nail bracket and a pair of band extensions affixed thereto, the band extensions being shown in an initial blank configuration.
Figure 16:
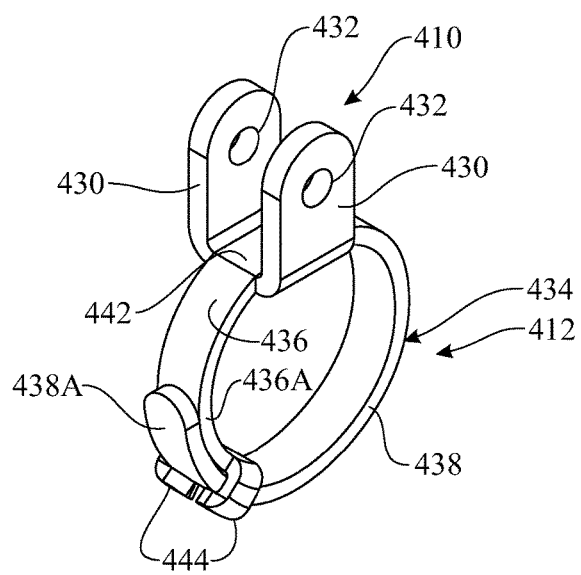
FIG. 16 presents an upper isometric view of the nail bracket with the band extensions affixed thereto being shown in a final configuration in the form of one of the anchoring rings.

In FIG. 14 the first and second band extensions 436, 438 of the band 434 are in an initial configuration in which they have a blank-type form, whereas in FIG. 16 the first and second band extensions 436, 438 of the band 434 now are in a final configuration in which they have been transformed into the form of the second anchoring ring 412. This transformation is accomplished by bending the first and second band extensions 436, 438 of the band 434 in opposite directions circumferentially around the finger 404 such that their respective free end portions 436A, 438A are brought together in an overlapping relationship with respect to one another. The free end portion 436A of the first band extension 436 has a pair of wings 444 formed thereon so as to protrude in opposite directions from opposite longitudinal edges of the first band extension 436. The wings 444 are configured to bend, such as by being crimped, in opposite directions around opposite longitudinal edges of the second band extension 438 so as to secure the band extensions 436, 438 to one another and circumferentially around the finger 404 proximally of the flexion deformity 402 of the finger 404 with the opposite free end portions 436A, 438A in the overlapped relationship. The nail bracket 410 and second anchoring ring 412 may be made from any suitable bendable or pliable material, for example a metal or plastic.

Figure 18:
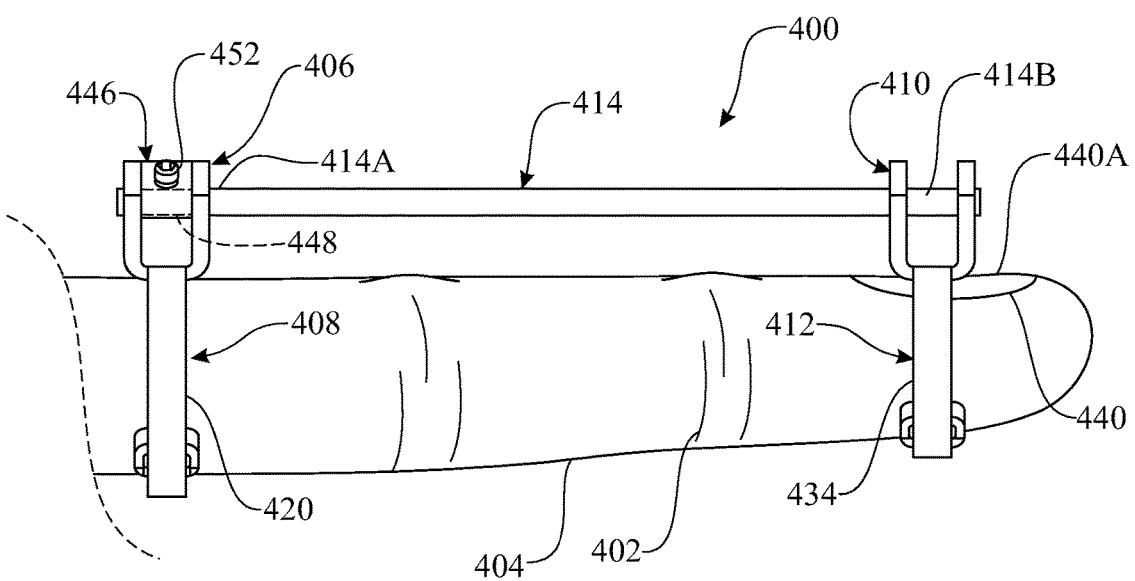
FIG. 18 presents a side elevation view of the splinting apparatus and system attached on the finger with the particular deformity.

As seen in FIGS. 13 and 18, the rigid connecting rod 414, being per se substantially the same as in the first and second implementations, is installed to extend between, and fixedly attach to at least one of, the phalangeal and nail brackets 406, 410. The connecting rod 414 at respective opposite end portions 414A, 414B thereof is received through the pairs of aligned apertures 418, 432 of the pairs of opposed side tabs 416, 430 of the phalangeal and nail brackets 406, 410. In such manner, the phalangeal and nail brackets 406, 410 are coupled in a spaced apart positional relationship to each other along the finger 404 relative to the flexion deformity 402 of the finger 404, with the phalangeal bracket 406 and respective first anchoring ring 408 being positioned proximally, and the nail bracket 410 and respective second anchoring ring 412 being position distally, of the flexion deformity 402 of the finger 404. The nail bracket 410 and an adjacent portion 412A of the second anchoring ring 412 are maintained closely adjacent to a top surface 440A of the finger nail 440 for adhering, such as gluing, by way of example but not limitation, the nail bracket 410 and the adjacent portion 412A of the second anchoring ring 412 to the top surface 440A of the finger nail 440. In the coupled spaced apart positional relationship, as seen in FIG. 18, the connecting rod 414 extends over the flexion deformity 402 in a spaced relationship thereto and the finger 404 is maintained in a substantially neutral or slight hyperextension position.

Preferably of the phalangeal and nail brackets 406, 410, only the phalangeal bracket 406 is fixedly attached to the one opposite end portion 414A of the connecting rod 414. The other opposite end portion 414B of the connecting rod 414 is slidably coupled to the opposed side tabs 430 of the nail bracket 410. The phalangeal bracket 406 has a body 446 disposed between its opposed side tabs 416. The body 446 exteriorly has a curved upper end surface 446A, a flat lower end surface 446B and a pair of planar opposite side surfaces 446C. The body 446 has a bore 448 extending therethrough and being open at its opposite exterior side surfaces 446C disposd adjacent to the opposed side tabs 430 of the phalangeal bracket 406 such that the bore 448 of the body 446 is in alignment with the aligned apertures 432 of the phalangeal bracket side tabs 430 and receives therethrough the respective one opposite end portion 414A of the connecting rod 414. At least one threaded hole 450 is formed in the body 446 so as to extend between, and being open at, the exterior upper end surface 446A of the body 446 and the bore 448 through the body 446. A set screw 452 is threadably inserted into the threaded hole 450 from the exterior upper end surface 446A of the body 446 into the bore 448 through the body 446 so as to contact the other opposite end 414B of the connecting rod 414 and hold the connecting rod 414 fixedly attached to the body 446 and thereby to the phalangeal bracket 406.

Figure 19:
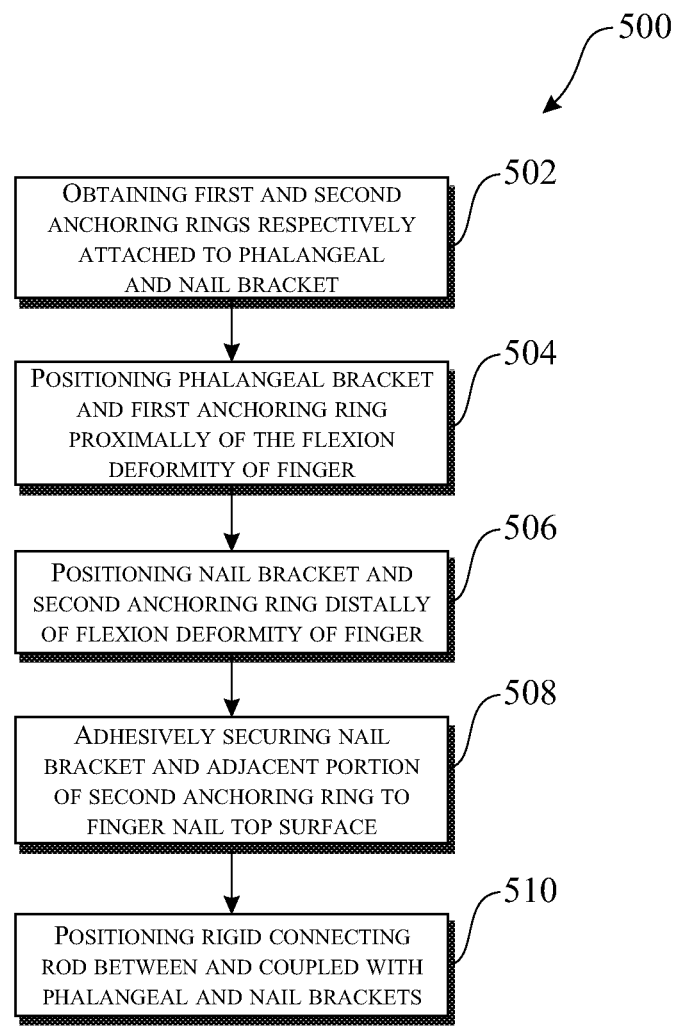
FIG. 19 presents a flow diagram of a second exemplary embodiment of a splinting method for treating a flexion deformity of a finger using the third implementation of the splinting apparatus and system in accordance with still another aspect of the present invention.

Referring now to FIG. 19, there is illustrated a flow chart, generally designated 500, showing in diagrammatical form a plurality of steps, which will now be briefly described with reference to the third implementation of the apparatus 400, that make up a splinting method, according to another aspect of the present invention, for treating the flexion deformity 402 of the finger 404. It should be understood that the steps of the method may occur in a different order with respect to each other than as described hereinafter.

Block 502 of flow chart 500 represents the steps of obtaining the first anchoring ring 408 fixedly attached to the phalangeal bracket 406, as seen in FIG. 15, and of obtaining the second anchoring ring 412 fixedly attached to the nail bracket 410, as seen in FIG. 14. Block 504 of flow chart 500 represents the step of positioning the phalangeal bracket 406 and the first anchoring ring 408 proximally of the flexion deformity 402 of the finger 404, by bending the first and second band extensions 422, 424 of the band 420 in opposite directions circumferentially about the finger 404 proximally of the flexion deformity 402 of the finger 404 and securing overlapping free end portions 422A, 424A of the first and second band extensions 422, 424 to one another so as to secure the first anchoring ring 408 about the finger 404. Block 506 of flow chart 500 represents the step of positioning the nail bracket 410 and the second anchoring ring 412 distally of the flexion deformity 402 of the finger 404 and closely adjacent to the nail 440 of the finger 404 by bending the first and second band extensions 436, 438 of the band 434 in opposite directions circumferentially about the finger 404 at the location of the finger nail 440 and distally of the flexion deformity 402 of the finger 404 and securing overlapping free end portions 436A, 438A of the first and second band extensions 436, 438 to one another so as to secure the second anchoring ring 412 about the finger 404. Block 508 of flow chart 500 represents the step of adhesively securing the nail bracket 410 and an adjacent portion 412A of the respective second anchoring ring 412 to the top surface 440A of the finger nail 440. Block 510 of flow chart 500 represents the step of positioning the rigid connecting rod 414 between the phalangeal and nail brackets 406, 410 and fixedly attaching the other opposite end portion 414B of the connecting rod 414 to the body 446 of the phalangeal bracket 406 so as to couple the phalangeal and nail brackets 406, 410 and the respective first and second anchoring rings 408, 412 therewith in the spaced apart positional relationship to each other respectively proximally and distally of the flexion deformity 402 of the finger 404. In such positional relationship, the connecting rod 414 is positioned over the flexion deformity 402 of the finger 404 in a spaced relationship thereto and the finger 404 is maintained in a substantially neutral or slight hyperextension position.

The implementation of the first and second apparatus 100, 200, while providing a system satisfactory for treating a flexion deformity of a finger, have been found to have certain drawbacks in the making of a stable, correct fit when utilizing the spring wire to secure the apparatus to the finger, namely, they are more time consuming than desired and requires extra practice to master the skill involved in making the stable, correct fit. With respect to the third apparatus 400, its implementation by use of the first and second anchoring rings 408, 412 formed from respective elongated narrow bands 420, 434, being no wider than the space between the opposed side tabs 416, 430 of the first and second anchoring rings 408, 412, and their mode of securement to the finger, as described hereinbefore, eliminates these drawbacks.

It should be mentioned that care should be taken not to compress the digital artery and nerve during performance of the above-described steps of the method. Also, the proximal end of the connecting rod 106, 206, 414 may be extended from the phalangeal bracket 102, 202, 406 to prevent the compensatory hyperextension of the Proximal interphalangeal (PIP) joint or Swan Neck Deformity. Also, additional components of the apparatus can be attached to include other digits, palm, wrist, and forearm in the splint.

In summary, the materials used in the splinting apparatus, method and system do not include hook-and-loop type fastening strips or adhesive tape, thereby allowing the skin to breath in open air and thus eliminating the chances of skin maceration and ulceration. The splinting apparatus, method and system may be tailored to meet a given patient's particular finger flexion deformity and therefore the type of fit that is required is to be expected. Removal of the splinting apparatus and system is not required for cleaning the apparatus or washing the patient's hand. The splinting apparatus, method and system allows a patient to wash the hand while it is on; thus risk of accidental loss of immobilization during washing is avoided. The splinting apparatus and system can be easily disassembled and re-assembled with use of a simple tool for follow-up clinical examination by the physician. The physician can provide this tool to the patient only when healing is established and removal of the splint is justified as a part of the treatment plan.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A splinting apparatus for treating a flexion deformity of a finger, comprising:
   a phalangeal bracket;
   a first anchoring ring fixedly attached to said phalangeal bracket and being configured for positioning said phalangeal bracket and respective first anchoring ring proximally of a flexion deformity of a finger;
   a nail bracket;
   a second anchoring ring fixedly attached to said nail bracket and being configured for positioning said nail bracket and respective second anchoring ring distally of the flexion deformity of the finger and closely adjacent to a nail of the finger; and
   a rigid connecting rod extending between, and fixedly attached to at least one of, said phalangeal and nail brackets so as to couple said phalangeal and nail brackets in a spaced apart positional relationship to each other along the finger relative to the flexion deformity of the finger with said phalangeal bracket and respective first anchoring ring being positioned proximally, and said nail bracket and respective second anchoring ring being positioned distally, of the flexion deformity of the finger;
   wherein said first and second anchoring rings are respective bands configured provided for being extendible circumferentially about the finger at respective positions proximally and distally of the flexion deformity of the finger such that said phalangeal and nail brackets and said respective first and second anchoring ring bands therewith are secured in said spaced apart positional relationship respectively proximally and distally of the flexion deformity of the finger, said nail bracket and an adjacent portion of said respective second anchoring ring band are maintained closely adjacent to the top surface of the finger nail for adhering said nail bracket and said adjacent portion of said respective second anchoring ring band to a top surface of the finger nail, said connecting rod extends over the flexion deformity of the finger in a spaced relationship thereto, and the finger is maintained in a substantially neutral or slight hyperextension position.

2. The apparatus of claim 1 wherein said phalangeal bracket comprises a pair of opposed side tabs being spaced apart from one another, each of said side tabs having an aperture defined therethrough such that said apertures are aligned with one another and a respective one of a pair of opposite end portions of said connecting rod is received through said aligned apertures of said side tabs of said phalangeal bracket.

3. The apparatus of claim 2 wherein said phalangeal bracket further comprises:
- a body disposed between said opposed side tabs and having a bore extending through said body and being open at opposite exterior side surfaces of said body disposed adjacent to said side tabs such that said bore is in alignment with said aligned apertures of said side tabs of said phalangeal bracket and receives therethrough said respective one opposite end portion of said connecting rod;
- at least one threaded hole extending between, and being open at, an exterior end surface of said body and said bore through said body; and
- a set screw inserted into said threaded hole from said exterior end surface of said body into said bore through said body so as to contact and hold said connecting rod fixedly attached to said body and thereby to said phalangeal bracket.

4. The apparatus of claim 2 wherein said side tabs of said phalangeal bracket have lower ends being spaced apart; and wherein said phalangeal bracket further comprises a bight rigidly attached to and extending between said lower ends of said side tabs.

5. The apparatus of claim 4 wherein said side tabs of said phalangeal bracket have substantially planar configurations and extend generally parallel to one another such that said phalangeal bracket has a substantially U-shaped configuration.

6. The apparatus of claim 4 wherein said first anchoring ring band comprises first and second band extensions rigidly attached to and extending in opposite directions from opposite ends of said bight of said phalangeal bracket and terminating in respective free end portions, said first and second band extensions being bendable in opposite directions circumferentially around the finger, said free end portion of one of said band extensions having a pair of wings thereon protruding in opposite directions from opposite longitudinal edges of said one band extension and configured to bend in opposite directions around opposite longitudinal edges of the other of said band extensions so as to secure said band extensions circumferentially around the finger with said free end portions of said band extensions in an overlapping relationship to one another.

7. The apparatus of claim 6 wherein said one of said band extensions having said pair of wings thereon is shorter in length than said other of said band extensions.

8. The apparatus of claim 2 wherein said first anchoring ring band comprises:
- a bight disposed between and attached to lower spaced apart ends of said side tabs of said phalangeal bracket; and
- first and second of band extensions extending in opposite directions from opposite ends of said bight and terminating in respective free end portions, said first and second band extensions being bendable in opposite directions circumferentially around the finger, said free end portion of one of said band extensions having a pair of wings thereon protruding in opposite directions from opposite longitudinal edges of said one band extension and configured to bend in opposite directions around opposite longitudinal edges of the other of said band extensions so as to secure said band extensions circumferentially around the finger with said free end portions of said band extensions in an overlapping relationship to one another.

9. The apparatus of claim 8 wherein said one of said band extensions having said pair of wings thereon is shorter in length than said other of said band extensions.

10. The apparatus of claim 1 wherein said nail bracket comprises a pair of opposed side tabs being spaced apart from one another, each of said side tabs having an aperture defined therethrough such that said apertures are aligned with one another and a respective one of a pair of opposite end portions of said connecting rod is received through said aligned apertures of said side tabs of said nail bracket.

11. The apparatus of claim 10 wherein said opposite side tabs of said nail bracket have lower ends being spaced apart; and wherein said nail bracket further comprises a bight rigidly attached to and extending between said lower ends of said side tabs.

12. The apparatus of claim 11 wherein said side tabs of said nail bracket have substantially planar configurations and extend generally parallel to one another such that said nail bracket has a substantially U-shaped configuration.

13. The apparatus of claim 11 wherein said second anchoring ring band comprises first and second band extensions rigidly attached to and extending in opposite directions from opposite ends of said bight of said nail bracket and terminating in respective free end portions, said first and second band extensions being bendable in opposite directions circumferentially around the finger, said free end portion of one of said band extensions having a pair of wings thereon protruding in opposite directions from opposite longitudinal edges of said one band extension and configured to bend in opposite directions around opposite longitudinal edges of the other of said band extensions so as to secure said band extensions circumferentially around the finger with said free end portions of said band extensions in an overlapping relationship to one another.

14. The apparatus of claim 13 wherein said one of said band extensions having said pair of wings thereon is shorter in length than said other of said band extensions.

15. The apparatus of claim 10 wherein said second anchoring ring band comprises:
- a bight disposed between and attached to lower spaced part ends of said side tabs of said nail bracket; and
- first and second band extensions rigidly attached to and extending in opposite directions from opposite ends of said bight and terminating in respective free end portions, said first and second band extensions being bendable circumferentially in opposite directions around the finger, said free end portion of one of said band extensions having a pair of wings thereon protruding in opposite directions from opposite longitudinal edges of said one band extension and configured to bend in opposite directions around opposite longitudinal edges of the other of said band extensions so as to secure said band extensions circumferentially around the finger with said free end portions of said band extensions in an overlapping relationship to one another.

16. The apparatus of claim 15 wherein said one of said band extensions having said pair of wings thereon is shorter in length than said other of said band extensions.

17. A method of treating a flexion deformity of a finger with a splinting apparatus, the method comprising the steps of:
obtaining a first anchoring ring fixedly attached to a phalangeal bracket;
obtaining a second anchoring ring fixedly attached to a nail bracket;
positioning the phalangeal bracket and first anchoring ring proximally of a flexion deformity of a finger by bending first and second band extensions of the first anchoring ring in opposite directions circumferentially about the finger proximally of the flexion deformity of the finger and securing overlapping free end portions of the first and second band extensions to one another so as to secure the first anchoring ring about the finger;
positioning the nail bracket and second anchoring ring distally of the flexion deformity of the finger and closely adjacent to a nail of the finger by bending first and second band extensions of the second anchoring ring in opposite directions circumferentially about the finger at the location of the finger nail and distally of the flexion deformity of the finger and securing overlapping free end portions of the first and second band extensions to one another so as to secure the second anchoring ring about the finger;
adhesively securing the nail bracket and an adjacent portion of the respective second anchoring ring to a top surface of the finger nail; and
positioning a rigid connecting rod between, and fixedly attaching the connecting rod to at least one of, the phalangeal and nail brackets so as to couple the phalangeal and nail brackets and the respective first and second anchoring rings therewith in a spaced apart positional relationship to each other respectively proximally and distally of the flexion deformity of the finger, dispose the connecting rod over the flexion deformity of the finger in a spaced relationship thereto, and maintain the finger in a substantially neutral or slight hyperextension position.

18. The method of claim 17 wherein said positioning the connecting rod between, and fixedly attaching the connecting rod to at least one of, the phalangeal and nail brackets further comprises:
fixedly attaching the connecting rod at one end portion thereof to the phalangeal bracket; and
slidably coupling the connecting rod at an opposite end portion thereof to the nail bracket.

19. A splinting system for treating a flexion deformity of a finger, comprising:
a phalangeal bracket comprising a pair of opposed side tabs each having an aperture defined therethrough such that said apertures are aligned with one another;
a first anchoring ring fixedly attached to said phalangeal bracket and being configured for positioning said phalangeal bracket and first anchoring ring proximally of a flexion deformity of a finger, said first anchoring ring comprising first and second band extensions rigidly attached to one another and to said opposed side tabs of said phalangeal bracket, said first and second band extensions extending in opposite directions from said phalangeal bracket and terminating in respective free end portions, said first and second band extensions being bendable in opposite directions circumferentially around the finger, said free end portion of one of said band extensions having a pair of wings thereon protruding in opposite directions from opposite longitudinal edges of said one band extension and configured to bend in opposite directions around opposite longitudinal edges of the other of said band extensions so as to secure said band extensions circumferentially around the finger, proximally of the flexion deformity of the finger, with said free end portions of said band extensions in an overlapping relationship to one another;
a nail bracket comprising a pair of opposed side tabs each having an aperture defined therethrough such that said apertures are aligned with one another;
a second anchoring ring fixedly attached to said nail bracket and being configured for positioning said nail bracket and second anchoring ring distally of the flexion deformity of the finger and closely adjacent to a nail of the finger, said second anchoring ring comprising first and second band extensions rigidly attached to one another and to said opposed side tabs of said nail bracket, said first and second band extensions extending in opposite directions from said nail bracket and terminating in respective free end portions, said first and second band extensions being bendable in opposite directions circumferentially around the finger, said free end portion of one of said band extensions having a pair of wings thereon protruding in opposite directions from opposite longitudinal edges of said one band extension and configured to bend in opposite directions around opposite longitudinal edges of the other of said band extensions so as to secure said band extensions circumferentially around the finger, distally of the flexion deformity of the finger, with said free end portions of said band extensions in an overlapping relationship to one another; and
a rigid connecting rod extending between, and fixedly attached to at least one of, said phalangeal and nail brackets, said connecting rod at respective opposite end portions thereof being received through said aligned apertures of said opposed side tabs of said phalangeal bracket and of said nail bracket so as to couple said phalangeal and nail brackets in a spaced apart positional relationship to each other along the finger relative to the flexion deformity of the finger with said phalangeal bracket and respective first anchoring ring being positioned proximally, and said nail bracket and respective second anchoring ring being positioned distally, of the flexion deformity of the finger;
wherein said nail bracket and an adjacent portion of said respective second anchoring ring are maintained closely adjacent to the top surface of the finger nail for adhering said nail bracket and said adjacent portion of said respective second anchoring ring to the top surface of the finger nail, said connecting rod extends over the flexion deformity of the finger in a spaced relationship thereto, and the finger is maintained in a substantially neutral or slight hyperextension position.

20. The system of claim 19 wherein said phalangeal bracket further comprises:
a body disposed between said opposed side tabs and having a bore extending through said body and being open at opposite exterior side surfaces of said body disposed adjacent to said side tabs such that said bore is in alignment with said aligned apertures of said side tabs of said phalangeal bracket and receives therethrough a respective one of said opposite end portions of said connecting rod;

at least one threaded hole extending between, and being open at, an exterior end surface of said body and said bore through said body; and a set screw threadably inserted into said threaded hole from said exterior end surface of said body into said bore through said body so as to contact and hold said connecting rod fixedly attached to said body and thereby to said phalangeal bracket.

\* \* \* \* \*